(12) United States Patent
McQueen et al.

(10) Patent No.: US 6,936,640 B2
(45) Date of Patent: Aug. 30, 2005

(54) BIGUANIDE/QUATERNARY AMMONIUM CONTAINING COPOLYMERIC BIOCIDES AND USE THEREOF IN PHARMACEUTICAL COMPOSITIONS

(75) Inventors: Nathaniel D. McQueen, Arlington, TX (US); Joonsup Park, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/992,300

(22) Filed: Nov. 18, 2004

(65) Prior Publication Data
US 2005/0124700 A1 Jun. 9, 2005

Related U.S. Application Data

(60) Provisional application No. 60/526,895, filed on Dec. 4, 2003.

(51) Int. Cl.[7] .................. A61K 31/155; C07C 279/26
(52) U.S. Cl. .................. 514/635; 564/233; 564/234; 564/235; 422/28; 429/78.04
(58) Field of Search .................. 514/635; 564/233, 564/234, 235

(56) References Cited

U.S. PATENT DOCUMENTS

| | | | |
|---|---|---|---|
| 2,325,586 A | 8/1943 | Bolton et al. | 260/2 |
| 2,643,232 A | 6/1953 | Rose et al. | 260/2 |
| 3,428,576 A | 2/1969 | Dickinson et al. | 260/2 |
| 3,808,224 A | 4/1974 | Didier et al. | 260/307 G |
| 5,260,385 A | 11/1993 | Iio | 525/328.2 |
| 5,629,385 A | 5/1997 | Kuo | 525/328.2 |
| 5,631,005 A | 5/1997 | Dassanayake et al. | 424/78.04 |
| 5,665,843 A | 9/1997 | Iio | 526/310 |
| 5,741,886 A | 4/1998 | Stockel et al. | 528/422 |
| 5,942,218 A * | 8/1999 | Kirschner et al. | 424/78.08 |
| 6,008,316 A | 12/1999 | Foster et al. | 528/229 |
| 6,180,093 B1 * | 1/2001 | De et al. | 424/78.04 |
| 6,319,464 B1 | 11/2001 | Asgharian | 422/28 |
| 6,369,112 B1 * | 4/2002 | Xia | 514/635 |
| 6,503,497 B2 | 1/2003 | Chowhan et al. | 424/78.04 |
| 6,664,294 B1 | 12/2003 | Park et al. | 514/635 |

FOREIGN PATENT DOCUMENTS

EP 0 411 111 2/1990

* cited by examiner

Primary Examiner—Peter G. O'Sullivan
(74) Attorney, Agent, or Firm—Gregg C. Brown

(57) ABSTRACT

Biguanide/quaternary ammonium compounds and the use of same as antimicrobial agents in pharmaceutical compositions are described. The biguanide/quaternary ammonium compounds are useful in the preservation of pharmaceutical compositions, particularly ophthalmic pharmaceutical compositions and compositions for treating contact lenses. The compounds are especially useful for disinfecting contact lenses.

10 Claims, No Drawings

BIGUANIDE/QUATERNARY AMMONIUM CONTAINING COPOLYMERIC BIOCIDES AND USE THEREOF IN PHARMACEUTICAL COMPOSITIONS

CLAIM FOR PRIORITY

This application claims priority from U.S. patent application Ser. No. 60/526,895, filed Dec. 4, 2003.

BACKGROUND OF THE INVENTION

The present invention is directed to biguanide/quaternary ammonium compounds having antimicrobial activity, and to the use of these compounds in pharmaceutical compositions. More specifically, the invention is directed to use of the subject biguanide/quaternary ammonium compounds in compositions and methods for disinfecting contact lenses, and to the use of these compounds to preserve various types of pharmaceutical compositions from microbial contamination, particularly ophthalmic, otic and nasal pharmaceutical compositions.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *Pseudomonas aeruginosa*, can lead to loss of the infected eye(s) if left untreated or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Polyhexamethylenebiguanide (PHMB) is a polymeric biguanide antimicrobial agent that is widely used in solutions for disinfecting contact lenses (e.g., ReNu™ Multi-Plus Multi-Purpose Solution marketed by Bausch & Lomb, Inc.). PHMB is a strong biocide, but is known to exhibit a high degree of toxicity at elevated concentrations. It is for this reason that lens care solutions containing PHMB use it at a concentration of 0.0001% or less, so as to avoid ocular irritation in the lens wearer. However, this concentration is not sufficient to give the disinfection level desired for FDA guidelines.

The polymeric quaternary ammonium compound known as "polyquaternium-1" has also been utilized extensively in disinfecting solutions and other products utilized to treat contact lenses (referred to herein as "CLC products"). While polyquaternium-1 exhibits relatively low toxicity, it does not exhibit the required antimicrobial activity against fungi (e.g., *Candida albicans*) in the presence of chloride-containing salts (e.g., NaCl and other anionic components commonly contained in CLC products.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material).

Many pharmaceutical compositions are required to be sterile (i.e., free of bacteria, fungi and other pathogenic microorganisms). Examples of such compositions include: solutions and suspensions that are injected into the bodies of humans or other mammals; creams, lotions, solutions or other preparations that are topically applied to wounds, abrasions, burns, rashes, surgical incisions, or other conditions where the skin is not intact; and various types of compositions that are applied either directly to the eye (e.g., artificial tears, irrigating solutions, and drug products), or are applied to devices that will come into contact with the eye (e.g., contact lenses).

The foregoing types of compositions can be manufactured under sterile conditions via procedures that are well known to those skilled in the art. However, once the packaging for the product is opened, such that the composition is exposed to the atmosphere and other sources of potential microbial contamination (e.g., the hands of a human patient), the sterility of the product may be compromised. Such products are typically utilized multiple times by the patient, and are therefore frequently referred to as being of a "multi-dose" nature.

Due to the frequent, repeated exposure of multi-dose products to the risk of microbial contamination, it is necessary to employ a means for preventing such contamination from occurring. The means employed may be (1) a chemical agent that prevents the proliferation of microbes in the composition, which is referred to herein as an "antimicrobial preservative"; or (2) a packaging system that prevents or reduces the risk of microbes reaching the pharmaceutical composition within a container.

Ophthalmic compositions generally must include an antimicrobial agent to prevent contamination of the compositions by bacteria, fungi and other microbes. Such compositions may come into contact with the cornea either directly or indirectly. The cornea is particularly sensitive to exogenous chemical agents. Consequently, in order to minimize the potential for harmful effects on the cornea, it is necessary to use anti-microbial agents that are relatively non-toxic to the cornea, and to use such agents at the lowest possible concentrations (i.e., the minimum amounts required in order to perform their anti-microbial functions).

Balancing the anti-microbial efficacy and potential toxicological activity of anti-microbial agents is sometimes difficult to achieve. More specifically, the antimicrobial agent concentration necessary for the preservation of ophthalmic formulations from microbial contamination or for the disinfection of contact lenses may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (e.g., antimicrobial preservation or disinfection).

The use of an inadequate level of antimicrobial preservation may create the potential for microbial contamination of the compositions and ophthalmic infections resulting from such contaminations. This is also a serious problem, since ophthalmic infections involving *pseudomonas aeruginosa* or other virulent microorganisms can lead to loss of visual function or even loss of the eye.

Thus, there is also a need for an improved means of preserving pharmaceutical compositions from microbial contamination. This need is particularly prevalent in the field of ophthalmic compositions. The antimicrobial agents utilized to preserve aqueous ophthalmic compositions must be effective in preventing microbial contamination of the compositions when used at concentrations that are non-toxic to ophthalmic tissues.

The present invention is directed to satisfying the above-cited needs.

SUMMARY OF THE INVENTION

The present invention is directed to certain biguanide/quaternary ammonium compounds having antimicrobial activity and to pharmaceutical compositions containing one or more of these compounds to preserve the compositions from contamination by microorganisms. The invention is also directed to the use of the subject biguanide/quaternary ammonium compounds to disinfect contact lenses.

The compounds of this invention contain both biguanide and quaternary ammonium moieties in order to capitalize on the strong antimicrobial properties of polymeric biguanides and the low cytotoxicity profile of polymeric quaternary ammonium compounds. The compounds exhibit stronger antimicrobial activity than polyquaternium-1, even in the presence of chloride or other anionic agents, yet are less toxic than PHMB. As a result, the compounds can be used at levels required to meet FDA disinfection or preservative efficacy criteria without causing significant ocular irritation or other ocular toxicity effects,

DESCRIPTION OF PREFERRED EMBODIMENTS

The biguanide/quaternary ammonium compounds of the present invention have the following formula:

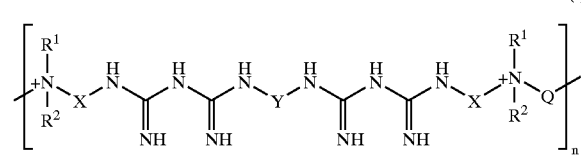

(I)

wherein:
n is a whole number of from 1 to 100;
$R^1$ and $R^2$ are the same or different and are selected from the group consisting of alkyl ($C_1$–$C_{10}$), aryl, and arylalkyl ($C_3$–$C_{16}$), all of which may optionally contain one or more heteroatoms;
X is selected from the group consisting of alkyl ($C_2$–$C_{12}$), aryl, and arylalkyl ($C_3$–$C_{12}$);
Y is selected from the group consisting of alkyl ($C_2$–$C_{16}$), aryl, and arylalkyl ($C_3$–$C_{12}$); and
Q is selected from the group consisting of alkyl ($C_2$–$C_{20}$), aryl, arylalkyl ($C_3$–$C_{20}$), amino alkyl ($C_2$–$C_{20}$), alkenyl ($C_2$–$C_{20}$), and alkylalkenyl ($C_4$–$C_{20}$), all of which may optionally contain one or more quaternary ammonium moieties or heteroatoms.

The present invention also encompasses pharmaceutically acceptable salts of the compounds of formula (I), above.

The preferred compounds of formula (I) are those wherein $R^1$ and $R^2$ are the same or different and are selected from the group consisting of alkyl ($C_1$–$C_6$) and arylalkyl ($C_3$–$C_{12}$), and Y is alkyl ($C_2$–$C_{12}$).

The most preferred compounds are those wherein: n is 1 to 20; $R^1$ and $R^2$ are methyl; X is propyl; Y is hexyl; and Q is alkyl ($C_2$–$C_{20}$), alkenyl ($C_2$–$C_{20}$), or alkylalkenyl ($C_4$–$C_{20}$), all optionally containing one or more quaternary ammonium moieties. Examples of such compounds are set forth in the following table:

| Compound Number | $R^1$, $R^2$ | X | Y | Q |
|---|---|---|---|---|
| 1 | $CH_3$ | propyl | hexyl | trans-2-butene |
| 2 | $CH_3$ | propyl | hexyl | Bis-(N,N-dimethyl-N-trans-2-butenyl)-1,12-diaminododecane |
| 3 | benzyl | propyl | hexyl | trans-2-butene |
| 4 | $CH_3$ | hexyl | hexyl | trans-2-butene |
| 5 | $CH_3$ | propyl | decyl | trans-2-butene |
| 6 | hydroxyethyl | propyl | hexyl | trans-2-butene |

The compounds of formula (I) may be synthesized in accordance with the following reaction scheme:

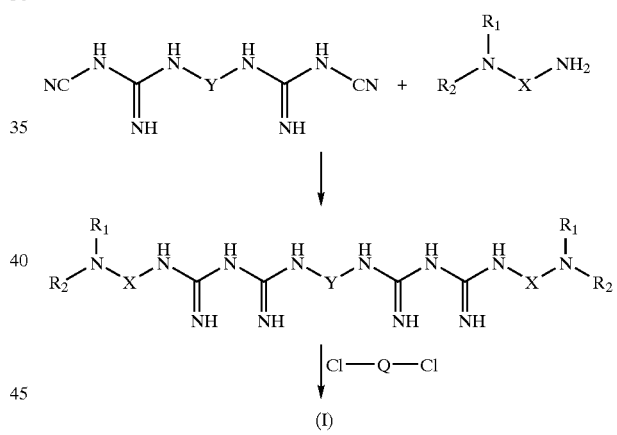

Suitable methods for synthesizing the compounds of formula (I) are further demonstrated by the following examples, which describe the synthesis of certain preferred compounds:

EXAMPLE 1

Synthesis of Compound Number 1

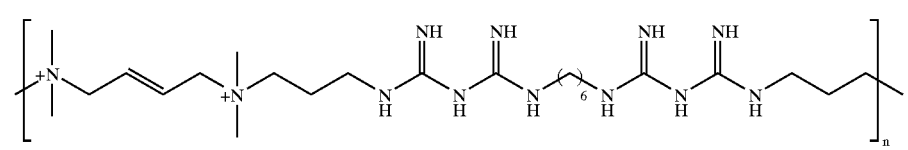

The compound identified in the foregoing table as "Compound Number 1", the structure of which is shown above, was synthesized as follows:

A mixture of 0.25 g (0.001 mol) of 1,6-dicyanoguanidinylhexane, 0.33 g (0.002 mol), of N,N-dimethylamino-N-propylamine 2 HCl. and 4 drops of N-methylpyrolidinone was reacted in a sealed vial at 158° C. for 5 hours. After cooling, the reaction mixture was dissolved in methanol and precipitated out with acetone. The residue was then deprotonated with diisopropylethylamine in ethanol and precipitated out with acetone to afford 0.300 g (56.9%) of an intermediate compound (referred to herein as "Intermediate 1"). 0.527 g (0.001 mol) of Intermediate 1 was dissolved in 20 ml ethanol and stirred for 5 hours with 2 g sodium bicarbonate. Then 0.25 g (0.002 mol) of trans-1,4-dichloro-2-butene was added and the reaction mixture was heated to 50° C. overnight under constant stirring. The mixture was centrifuged, and precipitated out with acetone to obtain 0.60 g (77%) of Compound 1. Elemental Analysis: Calcd. for $C_{52}H_{107}N_{24}Cl_8O_2$ (+5$H_2O$) (MW 1442.28): C, 43.30; H, 8.18; N, 23.30; Cl, 19.66. Found: C, 42.71; H, 8.48; N, 21.30; Cl, 19.49. NMR is consistent with structure.

EXAMPLE 2

Synthesis of Compound Number 2 microbial agents, chelating agents, buffering agents or tonicity agents), and the function of the compound(s) of formula (I) contained in the compositions (e.g., preservation of the compositions from microbial contamination, or disinfection).

The levels of antimicrobial activity required to preserve ophthalmic compositions from microbial contamination or to disinfect contact lenses are well known to those skilled in the art, based both on personal experience and official, published standards, such as those set forth in the United States Pharmacopoeia ("USP") and similar publications in other countries.

The concentrations determined to be necessary for the above-stated purposes can be functionally described as "an amount effective to disinfect" and "an amount effective to preserve" or variations thereof. The concentrations used for disinfection will generally be in the range of from about 0.0001 to about 0.1 percent by weight/volume ("w/v %"). The concentrations used for preservation will generally be in the range of from about 0.00001 to about 0.01 w/v %.

In addition to the compounds of formula (I) described above, the compositions of the present invention may contain one or more anti-microbial agents. The invention is not limited relative to the types of antimicrobial agents that may be utilized. The preferred biocides include: polyhexamethylene biguanide polymers ("PHMB"), polyquaternium-1,

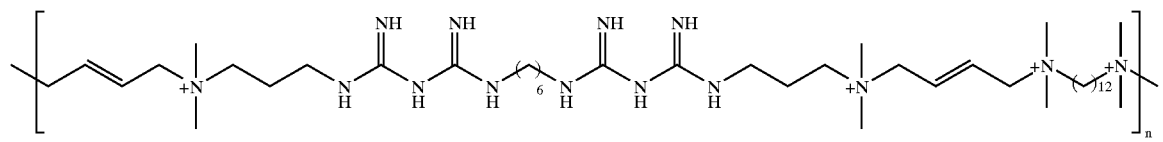

The compound identified in the foregoing table as "Compound No. 2", the structure of which is shown above, was synthesized as follows:

2.56 g (0.01 mol) of N,N,N',N'-tetramethyl-1,12-diaminododecane and 2.14 g (0.02 mol) of 1-chloro-4-hydroxy-t-2-butene were mixed together in 30 ml of isopropanol and heated to 50° C. for 5 hours under constant stirring. The reaction mixture was precipitated out with acetone to yield 4.6 g (97.9%) bisquat-diol compound. 0.470 g (0.001 mol) the bisquat-diol compound was then reacted with excess thionyl chloride, and precipitated out with diethyl ether. The supernatant was removed and the precipitate was dissolved in 5 ml of ethanol and added to a solution of 0.554 g (0.001 mol) of Intermediate 1 (see Example 1, above) that had stirred overnight in 15 ml ethanol in the presence of 2 g sodium bicarbonate. After addition, the reaction mixture was heated to 50° C. for 5 hours, followed by centrifugation and concentration in vacuo. The residue was then dissolved in ethanol and precipitated in acetone to yield 0.8 g (75.4%) of Compound 2. Elemental Analysis: Calcd. for $C_{44}H_{96}N_{14}Cl_6$ (+4$H_2O$) (MW 1106.12): C, 47.98; H, 9.48; N, 17.73; Cl, 19.23. Found: C, 47.67; H, 9.23; N, 18.27; Cl, 17.24. NMR is consistent with structure.

The amount of one or more compounds of formula (I) required to preserve particular formulations from microbial contamination or to disinfect contact lenses or other objects can be readily determined by persons skilled in the art. The concentration required will depend on the particular compound(s) of formula (I) selected, the presence or absence of other ingredients that have antimicrobial activity (e.g., antiand the amino biguanides described in co-pending U.S. patent application Ser. No. 09/581,952 and corresponding International (PCT) Publication No. WO 99/32158, the entire contents of which are hereby incorporated in the present specification by reference.

The most preferred amino biguanide is identified in U.S. patent application Ser. No. 09/581,952 as "Compound Number 1". This compound has the following structure:

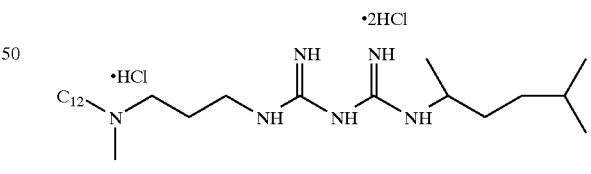

It is referred to below by means of the code number "AL-8496".

Amidoamines, amino alcohols, and borate/polyol complexes may also be utilized to enhance the antimicrobial activity of the compositions described herein. The preferred amidoamines are myristamidopropyl dimethylamine ("MAPDA") and related compounds described in U.S. Pat. No. 5,631,005 (Dassanayake, et al.). The preferred amino alcohols are 2-amino-2-methyl-1-propanol ("AMP") and other amino alcohols described in U.S. Pat. No. 6,319,464

(Asgharian). The entire contents of the '005 and '464 patents are hereby incorporated in the present specification by reference.

The compounds of formula (I) are preferably used in combination with borate or borate/polyol buffer systems. As used herein, the term "borate" includes boric acid, salts of boric acid, other pharmaceutically acceptable borates, and combinations thereof. The following borates are particularly preferred: boric acid, sodium borate, potassium borate, calcium borate, magnesium borate, manganese borate, and other such borate salts.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol and sorbitol. Especially preferred polyols are mannitol and sorbitol; most preferred is sorbitol.

The use of borate-polyol complexes in ophthalmic compositions is described in U.S. Pat. No. 6,503,497 (Chowhan); the entire contents of which are hereby incorporated in the present specification by reference. The compositions of the present invention preferably contain one or more borates in an amount of from about 0.01 to about 2.0% w/v, more preferably from about 0.3 to 1.2% w/v, and one or more polyols in an amount of from about 0.01 to 5.0% w/v, more preferably from about 0.6 to 2.0% w/v.

The compositions of the present invention may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyvinyl pyrrolidone and polyoxyethylene/polyoxypropylene copolymers), viscosity adjusting agents (e.g., hydroxypropyl methyl cellulose and other cellulose derivatives) and buffering agents (e.g., borates, citrates, phosphates and carbonates).

The compounds of formula (I) may also be included in various types of pharmaceutical compositions as preservatives, so as to prevent microbial contamination of the compositions. The types of compositions which may be preserved by the compounds of formula (I) include: ophthalmic pharmaceutical compositions, such as those described below; otic pharmaceutical compositions, such as topical compositions used in the treatment of bacterial infections or inflammation of the ear; dermatological compositions, such as anti-inflammatory compositions, as well as shampoos and other cosmetic compositions; and various other types of pharmaceutical compositions.

The present invention is not limited with respect to the types of pharmaceutical compositions in which the compounds of formula (I) may be contained as preservatives, but the compounds are particularly useful in preserving ophthalmic compositions from microbial contamination. The compounds are particularly useful in these types of compositions due to the ability of the compounds to exhibit a preservative effect at very low concentrations, without adversely affecting ophthalmic tissues.

The compounds of formula (I) may be included in various types of ophthalmic compositions to enhance anti-microbial activity. Examples of such compositions include: ophthalmic pharmaceutical compositions, such as topical compositions used in the treatment of glaucoma, infections, allergies or inflammation; compositions for treating contact lenses, such as disinfecting solutions, cleaning products, and products for enhancing the ocular comfort of patients wearing contact lenses; and various other types of compositions, such as ocular lubricating products, artificial tears, astringents, and so on. The compositions may be aqueous or non-aqueous, but will generally be aqueous.

The ophthalmic compositions of the present invention will be formulated so as to be compatible with the eye and/or contact lenses to be treated with the compositions. As will be appreciated by those skilled in the art, the ophthalmic compositions intended for direct application to the eye will be formulated so as to have a pH and tonicity that are compatible with the eye. This will normally require a buffer to maintain the pH of the composition at or near physiologic pH (i.e., 7.4) and may require a tonicity-adjusting agent (e.g., NaCl) to bring the osmolality of the composition to a level that ranges from slightly hypotonic to isotonic, relative to human tears. This range corresponds to an osmolality of from about 220 to about 320 milliosmoles per kilogram water ("mOsm/kg").

The formulation of compositions for treating contact lenses (e.g., disinfecting and/or cleaning) will involve similar considerations, as well as considerations relating to the physical effect of the compositions on contact lens materials and the potential for binding or absorption of the components of the composition to the lens. The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants (e.g., anionic surfactants, such as RLM 100; and nonionic surfactants, such as the polyxamines sold under the name "Tetronic®", particular by polyamide 1304, and the poloxamers sold under the name "Pluronic®"), viscosity adjusting agents and buffering agents, as described above.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compositions and methods of the present invention may be used in conjunction with various types of contact lenses, including both lenses generally classified as "hard" and lenses generally classified as "soft".

The following examples are provided to further illustrate the use of the compounds of formula (I) in pharmaceutical compositions and to demonstrate the antimicrobial activity of the compounds.

EXAMPLE 3

The following formulation represents an example of a contact lens disinfecting solution of the present invention. In this formulation, the biguanide/quaternary ammonium compounds of the present invention function to preserve the formulation from microbial contamination during storage. The compounds also function as an active disinfecting agent when the formulation is applied to contact lenses.

| Ingredient | Concentration (w/v %) |
|---|---|
| Compound | 0.0005 |
| Propylene Glycol | 0.5 |
| Sodium Chloride | 0.32 |
| Boric Acid | 0.6 |
| Tetronic 1304 ™ | 0.05 |
| Purified Water | q.s. 100 |
| HCl/NaOH | q.s. pH 7.8 |

In the foregoing formulation, the term "Compound" is intended to represent any of the biguanide/quaternary ammonium compounds of formula (I). The formulation is an aqueous, isotonic solution. The solution can be prepared by sequentially dissolving each ingredient in water, and adjusting the pH of the resulting solution, if necessary.

EXAMPLE 4

The following formulation represents another example of a contact lens disinfecting solution of the present invention:

| Ingredient | Concentration (w/v %) |
|---|---|
| Compound | 0.0005 |
| Boric Acid | 0.58 |
| Sodium Borate | 0.18 |
| Disodium EDTA | 0.05 |
| Sodium Chloride | 0.49 |
| Purified Water | q.s. 100 |
| NaOH/HCl | q.s. pH 7.0 |

The foregoing formulation is an aqueous, isotonic solution. It can be prepared in the same manner as the solution of Example 3 above.

EXAMPLE 5

The antimicrobial activity of the solution of Example 4, containing 0.0006 w/v 25% of the biguanide/quaternary ammonium compound identified above as Compound No. 1, was evaluated relative to three key microorganisms. The evaluation was conducted by determining the extent to which the solution reduced an initial population of about $10^6$/mL microorganisms over time. The results were as follows:

| Microorganism | $Log_{10}$ Reduction at 6 hours | $Log_{10}$ Reduction at 24 hours |
|---|---|---|
| Candida albicans | 2.7 | 3.8 |
| Serratia marcescens | 3.2 | 4.7 |
| Staphlococcus aureus | 6.0 | 6.0 |

These results demonstrate that the biguanide/quaternary ammonium compounds of formula (I) have potent antimicrobial activity.

EXAMPLE 6

The antimicrobial activity of the solution of Example 3, containing 0.0005 w/v % of Compound No. 2, was also evaluated using essentially the same procedure as those described in Example 5 above. The results were as follows:

| Microorganism | Log10 Reduction at 6 hours | Log10 Reduction at 24 hours |
|---|---|---|
| Candida albicans | 2.2 | 3.3 |
| Serratia marcescens | 4.1 | 6.3 |
| Staphlococcus aureus | 5.4 | 6.1 |

These results further demonstrate the potent antimicrobial activity of the biguanide/quaternary ammonium compounds of the present invention.

EXAMPLE 7

The antimicrobial activity of Compound No. 1 at a concentration of 0.0005 w/v % in water was also evaluated. The results were as follows:

| Microorganism | Log10 Reduction at 6 hours | Log10 Reduction at 24 hours |
|---|---|---|
| Candida albicans | 4.7 | 6.1 |
| Serratia marcescens | 4.8 | 6.1 |
| Staphylococcus aureus | 6.0 | 6.0 |

These results demonstrate that the antimicrobial activity of the solutions tested in Examples 5 and 6 above is attributable to the biguanide/quaternary ammonium compounds of the present invention (i.e., Compound No. 1 and Compound 2), rather than other components of the solutions described in Examples 5 and 6.

EXAMPLE 8

A test was conducted to evaluate the toxicity of Compound 1, relative to PHMB. Solutions containing Compound No. 1 and PHMB in the formulation described in Example 4 were tested in a neat/dilute neutral red uptake assay against MDCK target cells. A dose response was generated directly on the test plates by twofold serial dilution of the stock solutions. An initial 20 minute neat exposure was followed by 24 and 48 hour dilute exposures (1:10). The results under the headings "24ND50" and "48ND50"in the table below represent the concentrations of the test compounds that reduce neutral red uptake by 50% compared to a growth medium control after 24 hour and 48 hour exposures, respectively. The higher the concentration required, the less cytotoxicity the compound exhibited.

| Test Article | 24ND50 (ppm) | 48ND50 (ppm) |
|---|---|---|
| Compound 1 | 43 | 67 |
| PHMB | 16 | 21 |

The results demonstrate Compound 1 displays less cytotoxicity than PHMB at the same concentration.

EXAMPLE 9

The cytotoxicity of Compound 2 was compared to PHMB in the same manner and described in Example 8. The results are displayed in the table below:

| Test Article | 24ND50 (ppm) | 48ND50 (ppm) |
|---|---|---|
| Compound 2 | 74 | 77 |
| PHMB | 37 | 54 |

The results demonstrate that Compound 2 displays less cytotoxicity than PHMB.

What is claimed is:

1. A compound of the following formula:

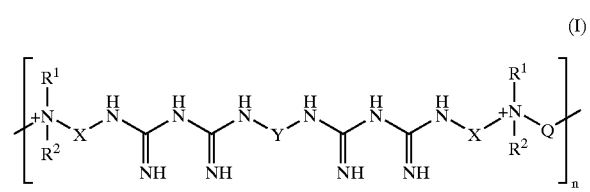

(I)

wherein:

n is a whole number of from 1 to 100;

$R^1$ and $R^2$ are the same or different and are selected from the group consisting of alkyl ($C_1$–$C_{10}$), aryl, and arylalkyl ($C_3$–$C_{16}$), all of which may optionally contain one or more heteroatoms;

X is selected from the group consisting of alkyl ($C_2$–$C_{16}$), aryl, and arylalkyl ($C_3$–$C_{12}$);

Y is selected from the group consisting of alkyl ($C_2$–$C_{16}$), aryl, and arylalkyl ($C_3$–$C_{12}$); and Q is selected from the group consisting of alkyl ($C_2$–$C_{20}$), aryl, arylalkyl ($C_3$–$C_{20}$), amino alkyl ($C_2$–$C_{20}$), alkenyl ($C_2$–$C_{20}$), and alkylalkenyl ($C_4$–$C_{20}$), all of which may optionally contain one or more quaternary ammonium moieties or heteroatoms; or a pharmaceutically acceptable salt thereof.

2. A compound according to claim 1, wherein $R^1$ and $R^2$ are the same or different and are selected from the group consisting of alkyl ($C_1$–$C_6$) and arylalkyl ($C_3$–$C_{12}$); and Y is alkyl ($C_2$–$C_{12}$).

3. A compound according to claim 2, wherein n is 1 to 20; $R^1$ and $R^2$ are methyl; X is propyl; Y is hexyl; and Q is selected from the group consisting of trans-2-butene and bis-(N,N-dimethyl-N-trans-2-butenylamino)dodecane.

4. A pharmaceutical composition comprising an amount of a compound of claim 1 effective to preserve the composition from microbial contamination.

5. A pharmaceutical composition according to claim 4, wherein the composition is an aqueous ophthalmic composition.

6. A pharmaceutical composition according to claim 4, wherein the composition is an aqueous otic composition.

7. A pharmaceutical composition according to claim 4, wherein the composition is utilized to treat contact lenses.

8. A composition for disinfecting contact lenses, comprising a disinfecting amount of a compound of claim 1, and an ophthalmically acceptable vehicle therefor.

9. A method of disinfecting a contact lens, which comprises applying the composition of claim 8 to the lens.

10. A method of preserving pharmaceutical compositions from microbial contamination, which comprises including a preservative effective amount of a compound of claim 1 in the composition.

* * * * *